United States Patent
Harder et al.

(10) Patent No.: US 9,072,497 B2
(45) Date of Patent: Jul. 7, 2015

(54) METHOD FOR AN IMAGE DATA ACQUISITION

(75) Inventors: Martin Harder, Nuremberg (DE); Dominik Paul, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 11 days.

(21) Appl. No.: 13/484,867

(22) Filed: May 31, 2012

(65) Prior Publication Data

US 2012/0310078 A1    Dec. 6, 2012

(30) Foreign Application Priority Data

May 31, 2011  (DE) .................. 10 2011 076 776

(51) Int. Cl.
*A61B 5/05*  (2006.01)
*A61B 5/00*  (2006.01)
*A61B 5/055*  (2006.01)

(52) U.S. Cl.
CPC ............... *A61B 5/742* (2013.01); *A61B 5/0555* (2013.01)

(58) Field of Classification Search
USPC .................................. 600/407–423
See application file for complete search history.

(56) References Cited

U.S. PATENT DOCUMENTS

| 6,529,762 | B1 | 3/2003 | Ladebeck |
| 2003/0139660 | A1 | 7/2003 | Tatebayashi et al. |
| 2008/0009708 | A1* | 1/2008 | Machida ............... 600/414 |
| 2009/0148020 | A1* | 6/2009 | Sugiura ............... 382/131 |

OTHER PUBLICATIONS

"Imaging Systems for Medical Diagnostics," Oppelt (2005), pp. 634-635.

* cited by examiner

*Primary Examiner* — Mark Remaly
(74) *Attorney, Agent, or Firm* — Schiff Hardin LLP

(57) ABSTRACT

A method for an image data acquisition with a magnetic resonance device that has a display unit includes acquisition of at least one overview measurement with at least one image data set, evaluation of the at least one image data set, generation of information of a slice geometry, graphical presentation of the information of the slice geometry along at least one slice plane, and acquisition of image data regarding a medical and/or diagnostic question and/or examination.

2 Claims, 4 Drawing Sheets

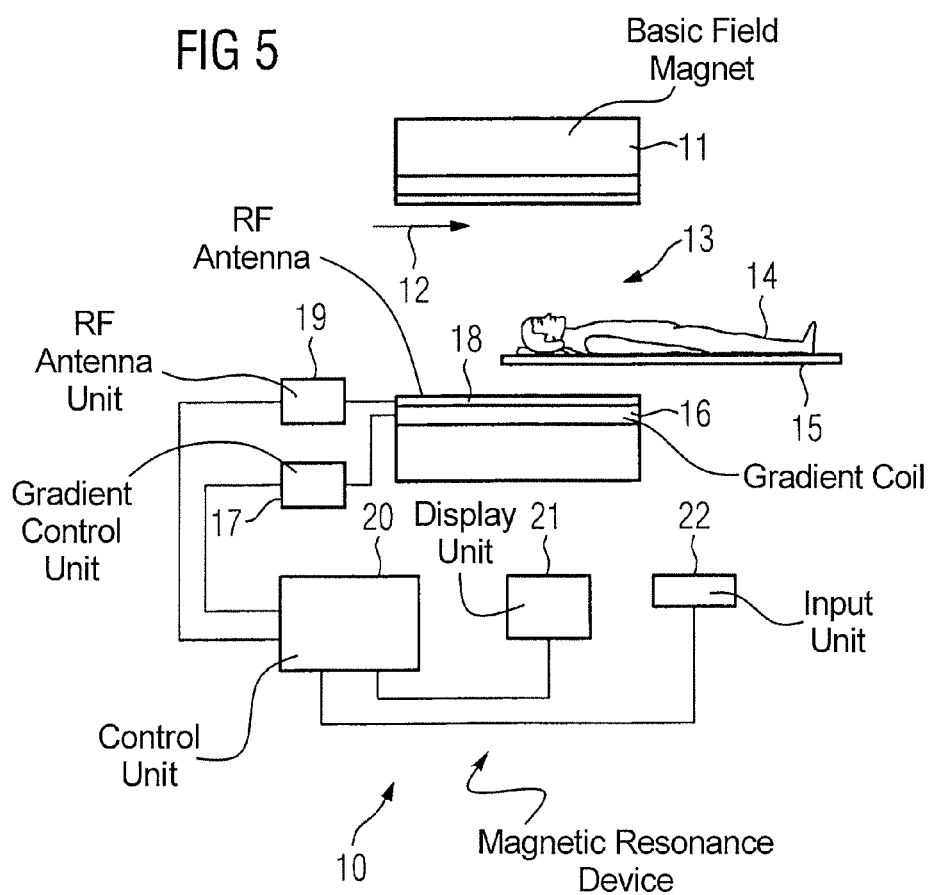

METHOD FOR AN IMAGE DATA ACQUISITION

BACKGROUND OF THE INVENTION

1. Field of the Invention

The present invention concerns a method to acquire image data with a magnetic resonance device that has a display unit.

2. Description of the Prior Art

For magnetic resonance examinations it is known to produce an overview measurement (data acquisition) before the examination (diagnostic) measurement (data acquisition), and to plan the slice geometry for the examination measurement using image data of the overview measurement. However, the slice geometry and/or information regarding the slice geometry are presented only in the form of a displayed and/or indicated section line for a slice in a two-dimensional presentation of an anatomical region of the patient. In such a presentation, the operator is not provided with planning certainty as to whether the indicated section line is tangential to or crosses a region relevant to the magnetic resonance examination. This can lead to the situation that the region of the patient that is relevant to a medical and/or diagnostic question and/or examination is not imaged or is only partially imaged by means of the magnetic resonance examination, and that the entire magnetic resonance examination as well as the overview measurement must be repeated.

SUMMARY OF THE INVENTION

An object of the present invention is to provide a method for an image data acquisition in which a high planning certainty for the magnetic resonance measurement is achieved.

This object is achieved in accordance with the invention by a method for an image data acquisition with a magnetic resonance device that has a display unit, including acquisition of at least one overview measurement with at least one image data set, evaluation of the at least one image data set, generation of information of the slice geometry, graphical presentation of the information of the slice geometry along at least one slice plane, and acquisition of image data regarding a medical and/or diagnostic question and/or examination.

A representation of the information of the slice geometry with regard to the region of the patient that is relevant to the medical and/or diagnostic question and/or examination can be achieved. In addition, a high planning certainty for the planning of acquisition of image data for the medical and/or diagnostic question and/or examination can be achieved by an operator (for example a clinical personnel interested with the magnetic resonance examination) being able to immediately recognize an incorrect planning, for example a slice curve that is disadvantageous for the acquisition of image data regarding the medical and/or diagnostic question and/or examination. As used herein, an "overview measurement" means a measurement occurring before the acquisition of image data regarding the medical and/or diagnostic question and/or examination, by means of which positioning of a treatment region and additionally planning and adjustment of a slice geometry for the acquisition of image data regarding the medical and/or diagnostic question and/or examination take place. The overview measurement has a spatial resolution that is lower than the spatial resolution of the measurement for the acquisition of image data regarding the medical and/or diagnostic question and/or examination. For example, the slice geometry and/or the information about the slice geometry can include the slice thickness, the attitude of the slice, the position of the slice and/or additional relevant parameters. The slice plane is formed by a plane in which the imaging slice is to be acquired.

The information of the slice geometry can be presented within a three-dimensional structure of a presented (displayed) examination region of the patient. The slice geometry and/or the slice plane can be represented particularly simply for the operator within the region that is relevant to the medical and/or diagnostic examination, so that the operator can implement a time-saving and exact planning of the slice geometry. The presentation of the information of the slice geometry within the three-dimensional structure preferably is a two-dimensional image of the three-dimensional structure, with the imaging plane of the two-dimensional image corresponding to the slice plane. The imaging plane or the slice plane can assume an arbitrary direction and/or position within the three-dimensional structure.

Furthermore, in accordance with the invention, a graphical presentation area can be generated to present the information of the slice geometry, and this graphical presentation area is presented by means of the display unit. A fast and comfortable reading and/or recognition of the information of the slice geometry can be achieved for the operator. A graphical presentation area in this context means a graphical user interface and/or a window that can be presented on a monitor. The graphical presentation area is configured so as to be designed exclusively for the presentation of the information of the slice geometry.

In an embodiment of the invention, at least two or more preview images are presented simultaneously by means of the graphical presentation area, so an advantageous overview can be achieved for the operator responsible for the magnetic resonance examination for the planning of the acquisition of image data regarding the medical and/or diagnostic question and/or examination. The presentation of the at least two or more preview images can take place side by side or one atop the other within the graphical presentation area. For this purpose, the graphical presentation area can include a menu function to switch and/or page between the individual preview images.

Furthermore, the slice plane for a presentation can be selected, and the information of the slice geometry is generated immediately after the selection of the slice plane and is graphically presented along this slice. Parameters for the slice geometry can be entered as inputs and/or the slice geometry can be selected by the operator in such a manner, and a preview of the selection can additionally be directly displayed to the operator in a next step after the operator's input, together with the three-dimensional structure. Incorrect plans can be recognized immediately, and if necessary a correction by the operator and/or a control unit can take place. Furthermore, changes in the slice geometry can be visually presented immediately in the form of a response to the inputs of the operator and/or online.

The invention also encompasses a magnetic resonance device with a control unit for an implementation of the method as described above.

BRIEF DESCRIPTION OF THE DRAWINGS

FIG. 5 schematically illustrates a magnetic resonance device according to the invention.

DESCRIPTION OF THE PREFERRED EMBODIMENTS

Figure 1:
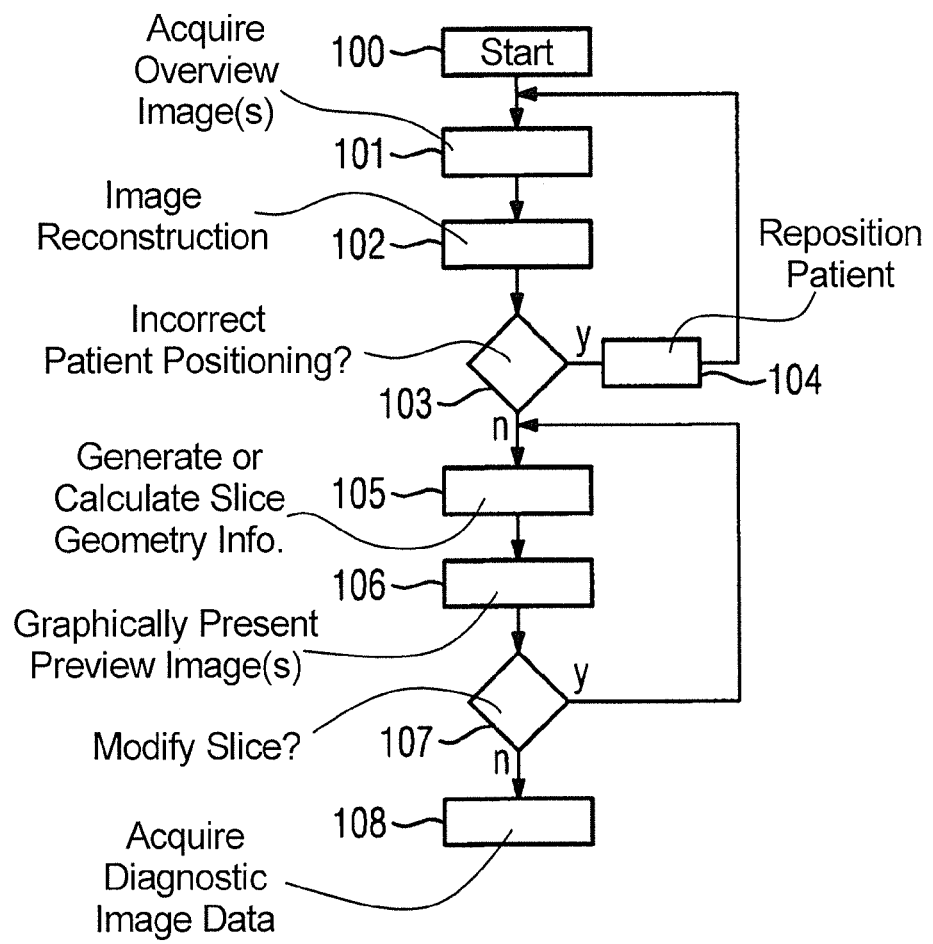
FIG. 1 is a flowchart of an embodiment of the method according to the invention for an image data acquisition.

A magnetic resonance device 10 according to the invention is shown in FIG. 5. The magnetic resonance device 10 has a basic field magnet 11 that generates a strong and constant basic magnetic field 12. The magnetic resonance device 10 also has a cylindrical acquisition region 13 to receive a patient 14. The acquisition region 13 is enclosed by the basic field magnet 11 in a circumferential direction. The patient 14 can be slid into the acquisition region 13 by means of a patient bed 15 of the magnetic resonance device 10. For this purpose, the patient bed 15 is arranged so as to be movable within the magnetic resonance device 10.

Furthermore, the magnetic resonance device 10 has a gradient coil 16 to generate magnetic field gradients that are used for spatial coding of the signals during an imaging. The gradient coil 16 is controlled by means of a gradient control unit 17. Furthermore, the magnetic resonance device 10 has a radio-frequency (RF) antenna 18 and a radio-frequency antenna unit 19 to excite a polarization that arises in the basic magnetic field 12 generated by the basic magnet 11. The radio-frequency antenna 18 is controlled by a radio-frequency (RF) antenna unit 19 and radiates radio-frequency magnetic resonance sequences into an examination space that is essentially formed by the acquisition region 13. The magnetization is thereby deflected out of its steady state. In addition, magnetic resonance signals are received by the radio-frequency antenna unit 19 via the radio-frequency antenna 18.

The magnetic resonance device 10 has the gradient control unit 17 to control the basic magnet 11 and a control unit 20 (formed by a computer) to control the radio-frequency antenna unit 19. The control unit 20 centrally controls the magnetic resonance device 10, for example the implementation of a predefined imaging gradient echo sequence. Control information—for example imaging parameters—as well as reconstructed magnetic resonance images can be displayed on a display unit 21 (for example on at least one monitor of the magnetic resonance device 10) to an operator of the magnetic resonance device 10. The magnetic resonance device 10 additionally has an input unit 22 by means of which information and/or parameters can be input by an operator during a measurement procedure. For example, the input unit 22 can comprise a keyboard and/or a computer mouse and/or additional input elements.

Naturally, the shown magnetic resonance device 10 can have additional components that magnetic resonance devices 10 conventionally have. In addition, a general functionality of a magnetic resonance device 10 is known to those skilled in the art, such that a more detailed description of the basic operation of the magnetic resonance device 10 is not necessary herein.

A method according to the invention for an image data acquisition by means of the magnetic resonance device 10 is presented in FIG. 1. The method is controlled by a control unit 20 of the magnetic resonance device 10 and predominantly runs independently or, respectively, automatically by means of the control unit 20 after a start signal 100 that is manually input by an operator (for example a clinical personnel interested with the magnetic resonance examination) of the magnetic resonance device 10 and/or is generated automatically by the control unit 20. Computer programs and additional software for this purpose are stored on a memory unit (not shown in detail) of the control unit 20, by means of which computer programs and additional software a processor (not shown in detail) of the control unit 20 automatically controls and/or executes a method workflow of the method for image data acquisition. At a start of the method it is necessary that the patient 14 is positioned within the acquisition region 13.

In this method for image data acquisition, at least one overview measurement 101 with at least one image data set is acquired as controlled by the control unit 20. Image data of the at least one image data set are subsequently evaluated in a reconstruction step 102. Information regarding a positioning of the patient 14 within the acquisition region 13 is determined automatically and/or independently in the reconstruction step 102 by the control unit 20. Insofar as the patient 14 is positioned incorrectly, this incorrect positioning 103 is detected by the control unit 20, and a repositioning 104 of the patient 14 within the magnetic resonance device takes place, wherein the repositioning 104 of the patient 14 is implemented independently and/or automatically by the control unit 20, for example in that the patient bed 15 together with the patient 14 is repositioned. If a repositioning 104 takes place after the reconstruction step 102, a new overview measurement 101 with at least one image data set is subsequently acquired automatically.

If no repositioning 104 of the patient 14 within the acquisition region 13 of the magnetic resonance device 10 is required, a generation 105 and/or calculation of information regarding a slice geometry and/or calculation of information regarding a slice geometry for the treatment region of the patient 14 takes place using the image data set. For example, this information of the slice geometry can include a slice position within the treatment region and/or an orientation of the slice within the treatment region and/or a thickness of the slice etc.

Figure 2:
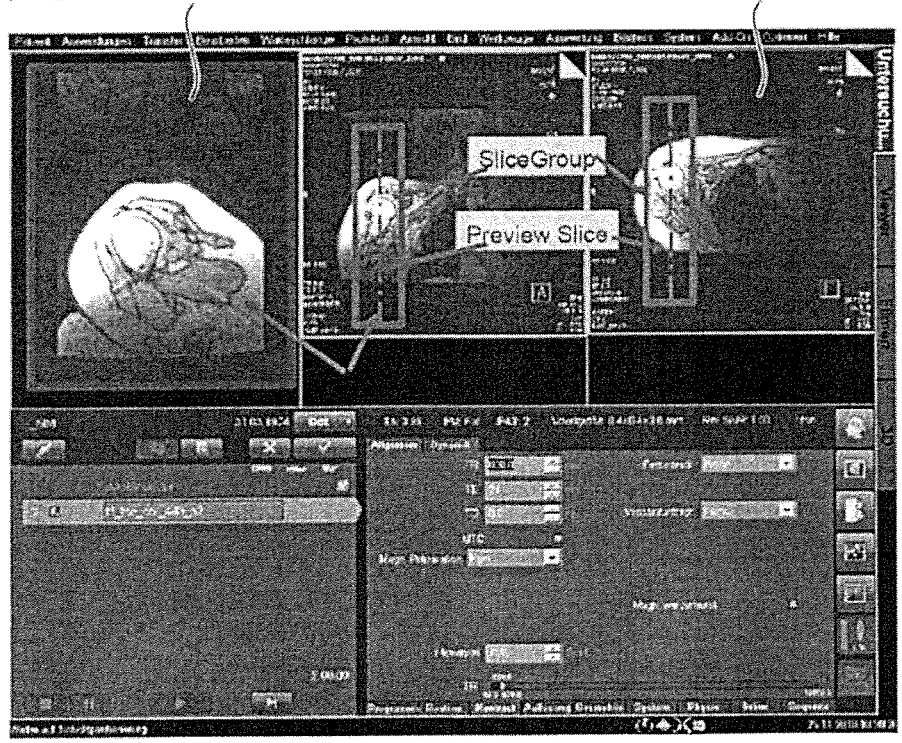
FIG. 2 shows a first representation along a slice plane.
Figure 3:
FIG. 3 shows a second representation along a slice plane.
Figure 4:
FIG. 4 shows a third representation along a slice plane.

Immediately after the generation and/or calculation of the information of the slice geometry in step 105, this information is graphically presented to the operator in the form of preview images by means of the monitor of the display unit 21 (FIGS. 2 through 4). For graphical presentation 106 of the preview images, a graphical presentation area 23, which is formed by a graphical user interface and/or a window that is presented by means of the monitor, is generated by the control unit 20. A presentation 106 of the preview images that depict the information of the slice geometry along at least one slice plane of the slice geometry takes place by means of the graphical presentation area 23. The slice plane of the slice geometry is presented within a three-dimensional structure of the region of the patient 14 that is relevant to the medical and/or diagnostic question and/or examination. This presentation is shown along the slice plane through the region of the patient 14 that is relevant to the medical and/or diagnostic question and/or examination.

Multiple individual slices for which a preview image is respectively created by the control unit 20 are frequently generated for the generation 105 of the slice geometry of the region of the patient 14 that is relevant to the medical and/or diagnostic question and/or examination. These preview images are presented simultaneously to the operator by means of the graphical presentation area 23, wherein the individual preview images are shown overlapping. For this purpose, the graphical presentation area 23 has a menu guide 24 by means of which the operator can page among the individual preview images by using the input unit 22 (for example a computer mouse of the input unit 22). In addition, it is also possible for the operator to select individual preview images for the presentation by the graphical presentation area 23 by means of the menu guide 24. As an alternative, it is also possible for the individual preview images to be shown at least partially side-by-side within the graphical presentation area 23.

At the same time, additional graphical presentation areas 25 and/or presentation elements are shown together with the graphical presentation area 23 on the display unit 21 (in particular the monitor), as is shown in FIGS. 2 through 4. These additional graphical presentation areas 25 and/or presentation elements are designed for a presentation of a three-dimensional image of the region that is relevant to the medical and/or diagnostic question and/or examination, for example, wherein the slice plane for the slice geometry is shown in the form of a drawn section line that is projected into the three-dimensional image.

In addition, by means of the additional graphical presentation areas 25 and/or presentation elements the operator has the possibility to make a selection with regard to the slice plane or multiple slice planes for the slice geometry in a next step, by the operator selecting and/or modifying the position of the projected section lines, for example. For example, the section lines can be arranged parallel to one another or radially around a rotation axis. The operator can select the section lines by arrangement thereof within the image, and/or individual parameters of the slice plane can be entered by the operator as numerical values. Insofar as a selection and/or a modification of the slice plane was made in step 107 by the operator, the new slice geometry is automatically calculated or generated 105 by the control unit 20 using the new and/or modified parameters, and a presentation 106 of a current preview that takes the new and/or modified parameters into account takes place in the graphical presentation area 23.

The medical and/or diagnostic magnetic resonance examination 108 to acquire image data regarding the medical and/or diagnostic question and/or examination takes place after completing the slice planning. Image data that have a significantly higher spatial resolution than the spatial resolution of the image data of the image data set for the diagnostic measurement 101 are acquired for the medical and/or diagnostic emetic resonance examination 108.

Although modifications and changes may be suggested by those skilled in the art, it is the intention of the inventors to embody within the patent warranted hereon all changes and modifications as reasonably and properly come within the scope of their contributions to the art.

We claim as our invention:

1. A method for an image acquisition with a magnetic resonance data acquisition device comprising a display unit, said method comprising:

from a control unit, operating said magnetic resonance data acquisition device, prior to operating said magnetic resonance acquisition device to acquire diagnostic magnetic resonance image data of a slice of an examination subject that is relevant for a medical or diagnostic question, to interact with the examination subject to acquire at least one image data set representing an overview scan of the examination subject in the magnetic resonance device;

supplying said at least one image data set to a computerized processor and, in said processor, reconstructing said overview scan from said at least one image data set and causing said overview scan to be visually displayed at said display unit;

using the displayed overview scan to identify information describing a slice geometry of said slice in a region of the subject that is relevant for said medical or diagnostic question, and providing said information to said processor;

from said processor, causing a graphical representation of said information to be displayed as at least one preview image that shows said information in relation to the displayed overview scan, along at least one slice plane of said slice;

from the displayed graphical representation of said information in relation to the displayed overview scan, selecting at least one selected designation, from the group consisting of said at least one slice plane and a slice geometry of said at least one slice plane, for operating said magnetic resonance data acquisition device to acquire image data to answer said medical or diagnostic question;

making said selected designation available to said processor and, in said processor, automatically calculating a new slice geometry from said selected designation and, from said processor, causing at least one further preview image to displayed that shows said new geometry in relation to said overview scan;

via said processor, allowing a user to accept or modify said new slice geometry in order to produce a final geometry, and providing said final geometry from said processor to said control unit; and providing said at least one parameter to said control unit and, from said control unit, operating said magnetic resonance data acquisition device according to said at least one parameter to again interact with said examination subject to acquire said image data from the examination subject for answering said medical or diagnostic question.

2. A magnetic resonance apparatus comprising:

a magnetic resonance data acquisition unit configured to receive a patient therein;

a control unit configured to operate said magnetic resonance data acquisition unit, prior to operating said magnetic resonance acquisition device to acquire diagnostic magnetic resonance image data of a slice of an examination subject that is relevant for a medical or diagnostic question, to acquire magnetic resonance data from said patient;

a display unit in communication with said control unit;

said control unit being configured to operate said magnetic resonance data acquisition unit to interact with the patient to acquire at least one image data set representing an overview scan of the patient in the magnetic resonance data acquisition unit;

said control unit comprising or communicating with a processor to which said at least one image data set is supplied and said processor being configured to reconstruct said overview scan from said at least one image data set and to cause said overview scan to be visually displayed at said display unit;

said processor also being provided with information, derived from the displayed overview scan describing a slice geometry of said slice in a region of the patient that is relevant for said medical or diagnostic question;

said processor being configured to cause a graphical representation of said information to be displayed as at least one preview image that shows said information in relation to the displayed overview scan, along at least one slice plane, of said slice in a display format that allows selection therefrom of at least one selected designation, from the group consisting of said at least one slice plane and a slice geometry of said at least one slice plane, for operating said magnetic resonance data acquisition unit to acquire image data to answer said medical or diagnostic question;

making said selected designation available to said processor and, in said processor, automatically calculating a new slice geometry from said selected designation and, from said processor, causing at least one further preview image to displayed that shows said new geometry in relation to said overview scan;

via said processor, allowing a user to accept or modify said new slice geometry in order to produce a final geometry, and providing said final geometry from said processor to said control unit; and said control unit being configured to operate said magnetic resonance data acquisition unit according to said final geometry to again interact with the patient to acquire said diagnostic image data from the patient for answering said medical or diagnostic question.

* * * * *